(12) United States Patent
Wenger et al.

(10) Patent No.: US 6,927,208 B1
(45) Date of Patent: Aug. 9, 2005

(54) CYCLOSPORIN WITH IMPROVED ACTIVITY PROFILE

(75) Inventors: Roland M. Wenger, Riehen (CH); Manfred Mutter, Preverenges (CH); Thomas Ruckle, Lausanne (CH)

(73) Assignee: Debiopharm S.A., Lausanne (CH)

( * ) Notice: Subject to any disclaimer, the term of this patent is extended or adjusted under 35 U.S.C. 154(b) by 0 days.

(21) Appl. No.: 09/720,923

(22) PCT Filed: Jun. 30, 1999

(86) PCT No.: PCT/IB99/01232

§ 371 (c)(1),
(2), (4) Date: Feb. 20, 2001

(87) PCT Pub. No.: WO00/01715

PCT Pub. Date: Jan. 13, 2000

(30) Foreign Application Priority Data

Jul. 1, 1998 (CH) .............................................. 1405/98

(51) Int. Cl.[7] ........................ A61K 38/12; A61K 38/13; A61K 45/00; A61K 47/00
(52) U.S. Cl. ............................. 514/9; 514/11; 530/402; 530/317
(58) Field of Search ....................... 514/9, 11; 530/317, 530/402; 424/278.1

(56) References Cited

U.S. PATENT DOCUMENTS

| 4,108,985 A | 8/1978 | Rüegger et al. |
| 4,210,581 A | 7/1980 | Rüegger et al. |
| 4,220,641 A | 9/1980 | Traber et al. |
| 4,288,431 A | 9/1981 | Traber et al. |
| 4,396,542 A | 8/1983 | Wenger |
| 4,441,644 A | 4/1984 | Farian |
| 4,554,351 A | 11/1985 | Wenger |
| 4,814,323 A | 3/1989 | Andrieu et al. |
| 5,767,069 A * | 6/1998 | Ko et al. ....................... 514/11 |
| 5,948,884 A | 9/1999 | Lüchinger |
| 6,444,643 B1 * | 9/2002 | Steiner et al. ................. 514/11 |

FOREIGN PATENT DOCUMENTS

| EP | 0 484 281 | 5/1992 |
| EP | 0484281 | 6/1992 |
| WO | WO 97 04005 A | 6/1997 |

OTHER PUBLICATIONS

Holmes, K. K. et al. (1996) "report of the NIH AIDS research program evaluation" pp. 1–40.*
S. O'Keefe et al., FK–506– and CsA–sensitive activation of the interleukin–2 promoter by calcineurin, Nature, vol. 357, pp. 692–694, 1992.
Papageorgiou C et al: "Anti HIV–1 Activity of a Hydrophilic Cyclosporin Derivative with improved Binding Affinity to Cyclophilin A" Bioorganic & Medicinal Chemistry Letters, vol. 6, No. 1, 1996, pp. 23–26, 497, XP000615812.

* cited by examiner

Primary Examiner—Karen Cochrane Carlson
Assistant Examiner—Samuel W. Liu
(74) Attorney, Agent, or Firm—Sturm & Fix LLP

(57) ABSTRACT

The invention relates to a novel cyclosporin, the pharmaceutical use thereof and a pharmaceutical composition containing it.

7 Claims, 3 Drawing Sheets

CYCLOSPORIN WITH IMPROVED ACTIVITY PROFILE

The present invention relates to a novel cyclosporin (Cs), the pharmaceutical use thereof and to a pharmaceutical composition containing it.

Cyclosporins are a class of cyclic poly-N-methylated undecapeptides having several pharmacological activities; in particular, they are immunosuppressants, anti-inflammatories, anti-parasitic agents, drug resistance suppressors (anti-MDR) and anti-viral agents. The first cyclosporin isolated from a fungal culture is cyclosporin A which is found in the natural state and which is represented by the following formula:

Structure of Cyclosporin A

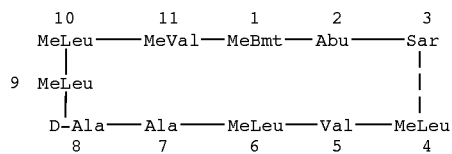

Abu=L-α-aminobutryic acid

Ala=L-alanine

MeBmt=N-methyl-(4R)-4-[(E)-2-butenyl]-4-methyl-L-threonine

Leu=L-leucine

MeLeu=N-methyl-L-leucine

MeVal=N-methyl-L-valine

Nva=L-norvaline

Sar=sarcosine

Thr=L-threonine

Val=L-valine

The amino acids described according to their conventional abbreviation have the configuration L unless otherwise specified.

Since this first cyclosporin was discovered, a large number of other varieties have been isolated and identified, as have non-natural varieties obtained by synthetic or semi-synthetic methods, or even by the application of modified culture techniques. The production of cyclosporin A is described by [Kobel et al. European Journal of Applied Microbiology and Biotechnology 14, 237–240 (1982)]. The production of artificial cyclosporins produced by a purely synthetic method developed by R. Wenger is also described—see Traber et al. 1, Traber et al. 2 and Kobel et al., U.S. Pat. Nos. 4,108,985; 4,210,581; 4,220,641; 4,288,431; 4,554,351 and 4,396,542; EP 34 567 and 54 782; WO 86/02080; Wenger 1, Transpl. Proc. 15, Suppl. 1:2230 (1983); Wenger 2, Angew. Chem.Int. Ed., 24,77 (1985); and Wenger 3, Progress in the Chemistry of Organic Natural Products 50, 123 (1986).

Cyclosporin A (CsA) isolated 20 years ago from *Tolypocladium inflatum* has considerable immunosuppressive activity. It has revolutionised organ transplantation and is commonly used in the treatment of autoimmune diseases. For a recent review of the use of CsA and its mechanisms of action, see Wenger et al; Cyclosporine Chemistry, Structure-activity relationships and Mode of Action, Progress in Clinical Biochemistry and Medicine, Vol. 2, 176 (1986).

The therapeutic effect of CsA results mainly in the selective suppression of the activation of T lymphocytes. This immunosuppressive activity is explained by the fact that CsA binds to an intracellular proteic receptor cyclophilin A (CyP), forming a CyP-CsA complex which interacts with calcineurin (CaN) and thus inhibits its phosphatase activity. Thus, the transcription of families of genes exhibiting precocious activation will be blocked (cf. O'Keefe, S. J; Tamura, J; *Nature* 1992, 357, 692–694).

The present invention provides the production of a novel cyclosporin with considerable HIV-1 (human immunodeficiency virus) inhibitory activity and not having the immunosuppressive activity of CsA.

The mode of infection of HIV type 1 is unique amongst the retroviruses because it requires the specific incorporation into its virion of the cellular protein CyP which interacts with the polyprotein Gag (cf. Eltaly Kara Franke, Bi-Xing Chem. Journal of Virology, September 1995, vol. 69 no. 9). It is well known that CyP binds to CsA and CaN in a ternary complex. However, the native function of CyP is to catalyse the isomerisation of peptidyl-prolyl bonds, a limiting and important step in the process allowing proteins to acquire a definitive three-dimensional structure. CyP also protects cells from thermal shocks or acts as a chaperone protein. Unlike CsA, the product of the Gag gene of HIV-1 prohibits the formation of a ternary complex with CyP and CaN. In fact, the HIV virus needs CyP in order to bind to the product of the Gag gene so as to form its own virions (cf. Franke, E. K; 1994 *Nature* 372, 359–362). In the presence of CsA, there is direct competition with the polyprotein derived from the Gag gene of HIV-1 to bind to CyP. This CsA acts at two levels on the replication of the viral cycle. Firstly, at the level of translocation towards the core of the pre-integrated complex, then in the production of infectious viral particles.

U.S. Pat. No. 4,814,323 already describes anti-HIV activity of CsA, but the latter also has considerable immunosuppressive activity which is undesirable for the treatment of patients infected with the HIV virus. Recently, another type of cyclosporin has been developed, namely derivatives in position 4 such as MeIle$^4$Cs, MeVal$^4$Cs, or (4-OH)MeLeu$^4$-Cs to mention only the most anti-HIV and the least immmunosuppressive substances. The derivative [(4-OH)MeLeu$^4$Cs] is synthesised by oxidation of cyclosporin A using a microorganism. Another patent WO 97/04005 uses the method of preparation of the patent EP 484 281 and the method developed by Seebach EP 194972 in order to produce derivatives in position 3 such as, for example, (D)-MeSer$^3$-(4-OH)MeLeu$^4$ cyclosporin. This substance has a better affinity for CyP but only has limited anti-HIV activity compared with the reference derivative MeIle$^4$-Cs (NIM 811). The more hydrophilic nature of this substance prevents it penetrating the cells and the organism. This is reflected directly in the reduced anti-HIV activity of this substance (cf. Christos Papageorgiou, J. J. Sanglier and René Traber—*Bioorganic & Medicinal Chemistry Letters*, Vol. 6, No. 1, pp. 23–26, 1996).

BRIEF DESCRIPTION OF THE DRAWINGS AND TABLES

Table I shows affinity results of Cs derivatives for cyclophilin A in a competitive ELISA test;

Table II shows the percentage protection during HIV infection of a CEM-SS cell line; and TABLE III shows examples of cyclosporins with different groups R1, R2, R3 and R4.

The substances described in this invention have the dual advantage of retaining the same affinity for CyP as that observed with [(4-OH)MeLeu⁴]-Cs or cyclosporin A whilst having anti-HIV activity which is identical to or greater than that of the reference derivatives (MeVal⁴-Cs or MeIle⁴-Cs) and appreciably greater than the anti-HIV activity of cyclosporin A or of (4-OH)MeLeu⁴-Cs. The object of the invention is to provide a novel cyclosporin which does not have the immunosuppressive activity of CsA and has an improved profile of activity. This new family of Cs is characterised by the formula (I):

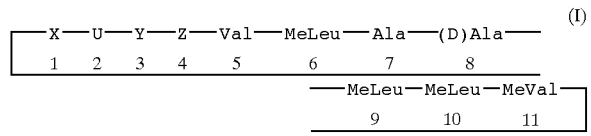

wherein:
X is -MeBmt or 6,7-dihydro-MeBmt-
U is -Abu, Nva, Val, or Thr
Y is Sar or (D)-MeSer or (D)-MeAla or (D)-MeSer (OAcyl)
Z is (N-R)aa where aa={Val, Ile, Thr, Phe, Tyr, Thr, (OAc), Thr (OG₁), Phe (G₂), PheCH₂(G₃), or Tyr (OG₃)} with R={alkyl>CH₃};
G₁={phenyl-COOH, phenyl-COOMe, or phenyl-COOEt};
G₂={CH₂COOH, CH₂COOMe(Et), CH₂PO(OMe)₂, or CH₂PO(OH)₂};
G₃={PO(OH)₂, PO(OCH₂CH=CH₂)₂, CH₂COOH, or CH₂COOMe(Et)}

Thus, by replacing the natural MeLeu group in position 4 by an N-(alkyl)aa group (where alkyl>CH₃), the anti-HIV 1 activity of this derivative is improved.

The new cyclosporin molecule thus obtained offers the unexpected and surprising advantage of having much better stability towards metabolisation than all the other cyclosporins known hitherto.

This new molecule is much more resistant to the phenomena of oxidation and degradation which take place in the cell. Consequently, the "in vivo" life of this new N-alkyl aa Cs is particularly prolonged.

Moreover, this new N-alkyl aa⁴ cyclosporin has high affinity for CyP and has anti-HIV activity which is equal to or greater than the best existing cyclosporins.

Figure 1:
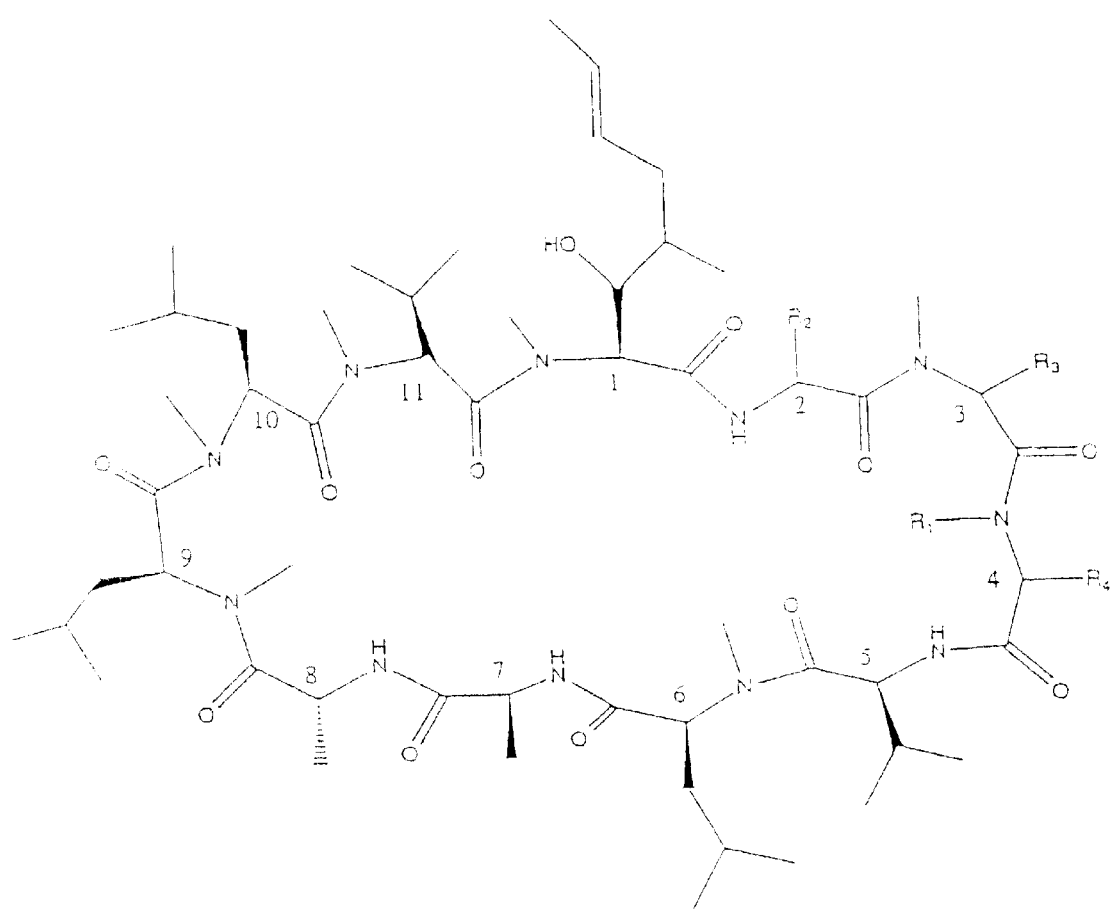
FIG. 1 shows the general structure of the novel cyclosporin according to the invention.
Figure 2:
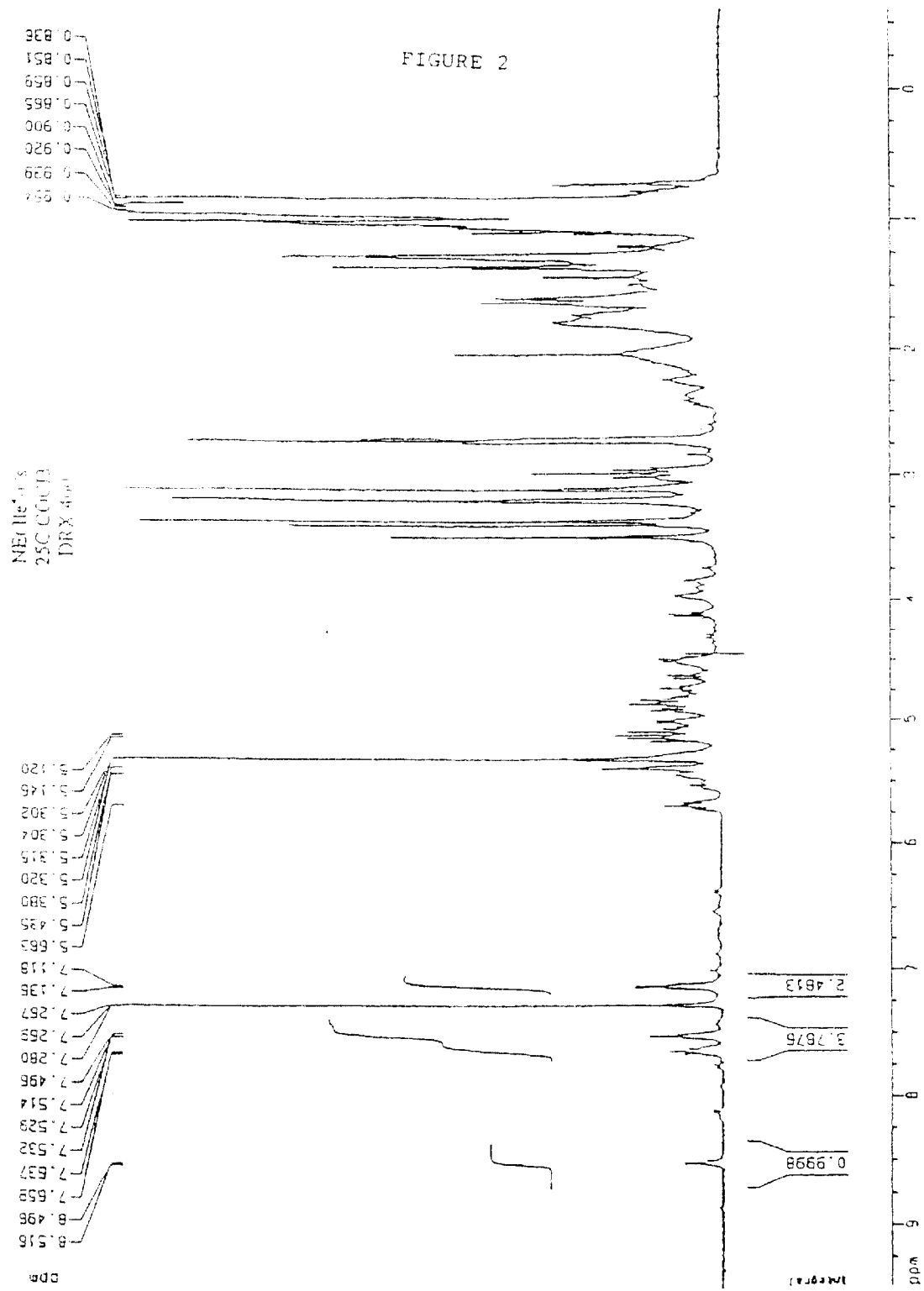
FIGS. 2 and 3 show analysis spectra for NEtIle4-Cs.
Figure 3:
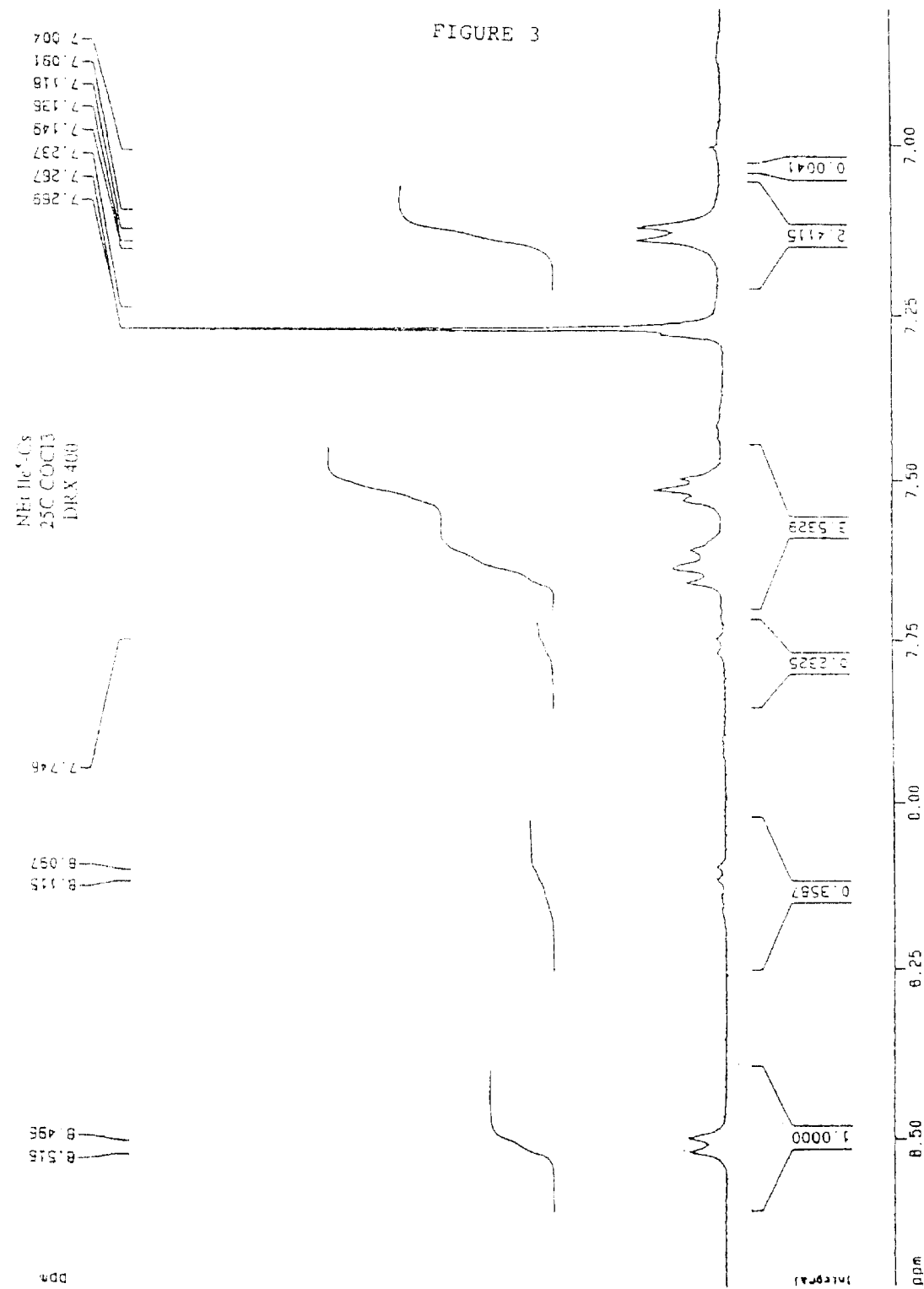

FIG. 1 represents the general structure of this novel cyclosporin. The groups R1, R2, R3 and R4 will be largely described in Table III. Thus, by transforming these 4 key positions, it was possible to retain a very good affinity for cyclophilin and to prevent the formation of a ternary complex with CaN and, above all, to increase, in a particularly advantageous manner, its stability towards enzymatic oxidation and consequently its anti-HIV activity.

This novel cyclosporin is thus characterised principally by the presence, in position 4, of a residue with R>CH₃ and R<C₁₀ H₂₁. The substituent of nitrogen used will be, for example, ethyl, propyl, butyl or pentyl, but these examples are not limiting. This novel cyclosporin is particularly active if the residue in position 4 is an N-ethylated amino acid (see drawings 2 and 3).

The invention also claims the pharmaceutical composition of the substance as described by formula (I). This may be combined with a pharmaceutically acceptable solution. The pharmaceutical formulation thus produced makes it possible to increase the solubility in water or to keep the composition in the form of microemulsions in suspension in water. The object of the present invention is also to provide a new medicinal product which may be used, for example, in the treatment and prevention of AIDS (acquired immunodeficiency syndrome). The cyclosporin modified in position 4 by a residue Z, namely N-ethyl-valine will be used in particular for the production of a medicinal product intended for the treatment and prevention of AIDS. The application for the prevention of AIDS is not limiting. This substance may also be used, for example, for its anti-inflammatory properties.

With regard to the process for the production of this novel cyclosporin, we used conventional techniques described in the literature and certain specific methods developed in the laboratory.

The process for the synthesis of CsA is described in: R. Wenger (Helv. Chim. Acta Vol. 67, p. 502–525 (1984)). The process for opening protected cyclosporin A (OAc) is described in Peptides 1996. The CsA molecule is treated with Meerwein's reagent (CH₃)₃OBF₄ then cleaved by treatment with acid in methanol or hydrolysed by water in order to convert it to a linear peptide of 11 amino acid residues: H-MeLeu-Val-MeLeu-Ala-(D)Ala-MeLeu-MeLeu-MeVal-MeBmt(OAc)-Abu-Sar-OCH3. This process was presented at the international conference of the European Society of Peptides (EPS-24) in Edinburgh 8–13 Sep. 1996 and published in Peptides 1996 by R. Wenger. This linear peptide is then treated according to the conventional Edman process in order to cleave its last amino acid residue (MeLeu) and to provide our starting product: the decapeptide H-Val-MeLeu-Ala-(D)Ala-MeLeu-MeVal-MeBmt (OAc)-Abu-Sar-OMe. This product is then used in the following steps:

Preparation of (1) (protection):
Boc-Val-MeLeu-Ala-(D)Ala-MeLeu-MeLeu-MeValMeBmt (OAc)-Abu-Sar-OMe (1)

0.72 ml (4.18 mmoles) of a solution of diisopropylethylamine and 0.65 g (2.95 mmoles) of Boc anhydride in 50 ml of dioxane are added to a solution of 2.83 g (2.46 mmoles) of the decapeptide H-Val MeLeu-Ala-(D)Ala-MeLeu-MeVal-MeBmt(OAc)-Abu-Sar-OMe in 120 ml of dioxane. 17 ml of water are added to the solution which is mixed for 2 hours at ambient temperature. The solvent is then evaporated and the resulting reaction mixture is dissolved in 300 ml of ethyl acetate then washed 3× with a 5% solution of citric acid, 3× with a saturated solution of NaHCO₃ and finally 3× with a solution of NaCl. The organic phases are dried with anhydrous Na₂SO₄, filtered, and the solvent is finally evaporated under vacuum. 3 g (98%) of the protected decapeptide (Boc-decapeptide methyl ester) are thus obtained.

The product is then used for the following synthesis routes without an additional purification step. This substance is hydrolysed then activated and condensed with 1 corresponding amino acid in order to produce a new peptide with 11 residues, the starting product for the cyclisation and production of a novel cyclosporin with the desired properties.

Preparation of (2) (hydrolysis of the ester):
Boc-Val-MeLeu-Ala-(D)Ala-MeLeu-MeLeu-MeValMeBmt (OAc)-Abu-Sar-OH (2)

192 mg (4.56 mmoles) of LiOH/H₂O dissolved in 36 ml of water are added dropwise (at 15° C.) to 4.08 g (3.26 mmoles) of the previous compound (1) in 146 ml of tetrahydrofuran. The whole mixture is stirred at 15° C. The reaction is complete after 120 hours after the successive addition of 5 portions respectively of 1.4 equivalents of LiOH/H₂O each. The solution obtained is neutralised with 0.1 N HCl and the solvent is then evaporated. The solid product recovered is then dissolved in 500 ml of ethyl acetate and washed 2× with a 5% solution of citric acid and 2× with a brine solution. The aqueous phases are extracted 4× with 50 ml of ethyl acetate and the combined organic phases are then dried with anhydrous $Na_2SO_4$, filtered and evaporated. 3.84 g (95%) of compound (2) are thus obtained. The product is then used without additional purification.

Preparation of (3) (addition of a new amino acid):
Boc-Val-MeLeu-Ala-(D)Ala-MeLeu-MeLeu-MeVal-MeBmt(OAc)-Abu-Sar-EtVal-OtBu (3)

6.18 g (5 mmoles) of compound (2) are dissolved in 250 ml of anhydrous dichloromethane under argon. The solution is then cooled and 3.9 ml of N-methylmorpholine (10 mmoles; pH 8.5) and 1.1 ml (10 mmoles) of isobutylchloroformate are then added slowly under argon. The solution is stirred for 15 minutes at −15° C. A solution of 2.4 g (12 mmoles) of H-NEt Val-OtBu dissolved in 40 ml of anhydrous dichloromethane is then added within a period of 20 minutes. The mixture is then stirred for 1 hour at −15° C., then for 1 hour at 0° C. and finally overnight at ambient temperature. 400 ml of dichloromethane are then added, then 3 extractions are carried out with a 5% solution of citric acid followed by 3 extractions with a saturated solution of $NaHCO_3$ and finally 3 final extractions with a saturated solution of NaCl. The organic phases are dried with anhydrous $Na_2SO_4$ then filtered and finally the solvent is evaporated. After chromatography, 4.42 g (62%) of pure undecapeptide are recovered.

Preparation of (4) (deprotection):
H-Val-MeLeu-Ala-(D)Ala-MeLeu-MeLeu-MeVal-MeBmt(OAc)-Abu-Sar-EtVal-OH (4)

830 mg (0.58 mmole) of protected undecapeptide (4) are dissolved in 15 ml of pure dichloromethane. 3.2 ml of trifluoroacetic acid are added to this solution within a period of 3 minutes at ambient temperature. The reaction is monitored by HPLC which proves to be complete after 1 h 30. The solvent is evaporated and the remaining trifluoroacetic acid is evaporated 2× in the presence of ethyl acetate.

The crude product (900 mg) is purified by chromatography [150 g of silica gel (0.4–0.63)], use of dichloromethane/methanol/triethylamine (17:3:0.05) as eluants) to eluate 700 mg (95%) of pure, deprotected undecapeptide (4).

Preparation of (5) (cyclisation):
MeBmt(OAc)$^1$-EtVal$^4$-Cs (5)

275 mg of TFFH (1.04 mmoles) are dissolved under argon in 3.45 l of anhydrous dichloromethane. The deprotected undecapeptide (4) [438 mg (0.347 mmole)] is then dissolved in 40 ml of anhydrous dichloromethane, and 0.52 ml (3.82 mmoles) of collidine are added thereto. This slightly basic peptide solution is added dropwise to the solution of TFFH within a period of 20 minutes under argon and with vigorous stirring. After 1 h 30 all the starting material is cyclised. In order to trap the excess TFFH, 5 ml of water are added, then the solution is evaporated. 200 ml of dichloromethane are added then the whole mixture is washed respectively 3× with a 0.1 N solution of aqueous HCl, 3× with a brine solution then dried with $Na_2SO_4$, filtered, and the solvent is evaporated. 360 mg of a yellowish oil are obtained. The crude product is purified by chromatography on silica gel using 100 g of silica gel (0.04–0.063 mm) and 1% of methanol in ethyl acetate as eluant. 230 mg (54%) of the pure derivative (5) are thus produced.

Cleavage of the MeBmt (OAc)-EtVal$^4$-Cs (5) acetate group and production of EtVal$^4$-Cs (6):

1.44 ml of a 0.45 molar solution of $NaOCH_3$ in MeOH (0.647 mmole) are added dropwise, under argon, to a solution of 700 mg (0.562 mmole) of the derivative of Cs (5) in 28 ml of MeOH. [The solution of $NaOCH_3$ in methanol is prepared by adding sodium to pure MeOH.] The reaction is complete after 48 h with stirring at ambient temperature. The mixture is adjusted to pH 5 by adding 50% acetic acid in water. The solvents are removed under vacuum. The crude product is dissolved in 200 ml of ethyl acetate and extracted 2× with water. The aqueous phase is re-extracted with 50 ml of ethyl acetate then the combined organic phases are washed 2× with a brine solution, dried with $Na_2SO_4$, filtered and the solvent is evaporated.

The product obtained (750 g) is chromatographed on 180 g of silica gel (0.04–0.063 mm) using a solution of acetone/hexane 1:1 (20 ml fractions). 550 mg (82%) of (EtVal$^4$)Cs (6) are thus produced.

Preparation of H-EtVal-Ot-Bu:

4.1 ml (23.83 mmoles) of diisopropylethylamine are added, under argon, to a suspension of 5 g (23.8 mmoles) of H-ValOtBu×HCl in 1 l of trimethyloxoformate. At the end of 10 minutes the suspension becomes clear. 13.5 ml (0.24 mmole) of acetaldehyde dissolved in 30 ml of trimethyloxoformate are added dropwise to this solution under anhydrous conditions. The reaction mixture is stirred for 45 minutes under argon at ambient temperature.

Using a low vacuum, the excess acetaldehyde is removed by evaporation for 1 h 30. 25 g (0.112 mmole) of solid $NaBH(OAc)_3$ are added, under argon, to this solution. After 15 minutes, the solution is cooled to 0° C. and 500 ml of a 2% aqueous solution of HCl are added slowly.

The trimethyloxoformate is evaporated under vacuum and the remainder of the aqueous solution is diluted in 300 ml of water. This solution is then extracted 2× with 100 ml of diethylether. The organic phase is then re-extracted 3× with a 0.1 N aqueous solution of HCl. The combined aqueous phases are cooled to 0° C. then the pH is adjusted to 9 using (2N)NaOH. The solution then becomes cloudy. The aqueous suspension is extracted 4× with 100 ml of diethylether. The combined organic phases are then dried with $Na_2SO_4$, filtered and the solvent is finally evaporated.

4.2 g of a yellowish oil resulting from this step are purified by chromatography using 900 g of silica gel (0.04–0.063 mm) and a mixture of hexane/ethyl acetate 8:2 as eluant. Finally, 3.13 g (65%) of pure H-EtLeu-OtBu are obtained.

The results of Table 1 show the affinity of the derivatives of Cs for cyclophilin A in a competitive ELISA test described by Quesniaux in Eur. J. Immunology 1987, 17, 1359–1365. In this test, during incubation with cyclophilin, Cs bound to BSA (serum albumin) is added to the Cs to be tested. The concentration required to obtain 50% inhibition ($IC_{50}$) of the reference reaction in the absence of competitor is then calculated. The results are expressed by the binding index BI which is the ratio of the $IC_{50}$ of the derivative and the $IC_{50}$ of CsA. A binding index (BI) of 1.0 indicates that the compound tested binds as well as CsA. A value lower than 1.0 indicates that the derivative binds better than CsA, and a value greater than 1.0 means that the derivative binds less well to CyP than CsA.

| Substance | Structure | BI | IR |
|---|---|---|---|
| UNIL 001 | CsA | 1.0 | 1.0 |
| UNIL 002 | MeVal$^4$-Cs | 0.6 | >200 |
| UNIL 004 | EtVal$^4$-Cs | 1.0 | >200 |
| UNIL 007 | MeIle$^4$-Cs | 0.5 | >200 |
| UNIL 013 | EtIle4-Cs | 1.3 | >200 |
| UNIL 014 | EtPhe(4-$CH_2PO(OMe)_2$)-Cs | 0.5 | >200 |

Cs is regarded as being immunosuppressive if its activity in the mixed lymphocyte reaction (MLR) is greater than 5%. The reaction (MLR) is described by T. Meo in "Immunological Methods", L. Lefkovits and B. Devis, Eds, Académie Prev. N.Y. pp: 227–239 (1979).

Spleen cells ($0.5.10^6$) originating from Balb/c mice (female, 8 to 10 weeks) are co-incubated for 5 days in the presence of treated spleen cells originating from CBA mice (females, 8 to 10 weeks). These cells were treated with mitomycin C or were irradiated at 2000 rads. The non-irradiated allogenic spleen cells exhibit a proliferative response in Balb/c cells which can be measured by incorporating a labelled precursor in the DNA. If the stimulator cells are irradiated (or treated with mitomycin C), the Balb/c cells no longer exhibit a proliferative response but retain their antigenicity. The $IC_{50}$ calculated in the MLR test is compared with the $IC_{50}$ corresponding to CsA in a parallel experiment. The IR index is thus found, this being the ratio of the $IC_{50}$ of the MLR test of the derivatives over the $IC_{50}$ of cyclosporin A.

As with the binding index (BI) above, a value of 1.0 for the IR means an activity similar to CsA. Similarly, a lower value means better activity and a value greater than 1.0 shows that the activity of the compound is lower than that of CsA.

An IR value of >20 shows that the substance is not immunosuppressive. The immunosuppression values of the derivatives are given in Table I.

Table II describes the percentage protection during infection with HIV of a CEM-SS cell line. The protection of this line in the presence of a Cs derivative is compared with the infection of a line cultivated in the absence of Cs (reference control). A mean value is established at a concentration of the derivative of $2 \times 10^{-6}$ molar. This anti-HIV activity was measured by the NCI (National Cancer Institute) in Washington in the USA.

| Substance | Structure | Percentage HIV Protection |
|---|---|---|
| UNIL 002 | MeVal$^4$-Cs | 66.4 |
| UNIL 004 | EtVal$^4$-Cs | 74.9 |
| UNIL 007 | MeIle$^4$-Cs | 68.5 |

A better percentage of protection against HIV infection obtained with the compound EtVal$^4$-Cs (compared with the two other references known to be 10× better than CsA) shows the advantage of substitution by N-ethyl in position 4. This remark is even more pertinent if one compares the affinity for CyP of each substance. An affinity for CyP similar to that of CsA (BI=1.0) is obtained for the EtVal$^4$-Cs derivative, whereas the derivatives MeVal$^4$-Cs and MeIle$^4$-Cs exhibit greater affinity for CyP (BI=0.6 and 0.5 respectively). A greater anti-HIV activity corresponds to a lower affinity for CyP of EtVal$^4$-Cs. This clearly shows the value of this novel derivative.

TABLE III

| Substance | $R_1$ | $R_2$ | $R_3$ | $R_4$ | $[\alpha]_n^{20}$ |
|---|---|---|---|---|---|
| EtVal$^4$CS | —CH$_2$CH$_3$ | CH$_2$CH$_3$ | —H |  | c = 0.07, MeOH −177 |
| EtIle$^4$CS | —CH$_2$CH$_3$ | CH$_2$CH$_3$ | —H | 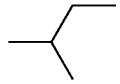 | c = 0.05, MeOH −204 |
| EtThr$^4$CS | —CH$_2$CH$_3$ | CH$_2$CH$_3$ | —H |  | |
| EtPhe$^4$CS | —CH$_2$CH$_3$ | CH$_2$CH$_3$ | —H | 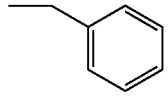 | c = 0.24, MeOH −159 |
| EtTyr$^4$CS | —CH$_2$CH$_3$ | CH$_2$CH$_3$ | —H | 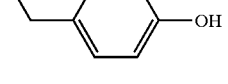 | |
| MePhe$^4$CS | —CH$_3$ | CH$_2$CH$_3$ | —H | 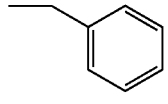 | c = 0.06, MeOH −134 |
| MeTyr$^4$CS | —CH$_3$ | CH$_2$CH$_3$ | —H | 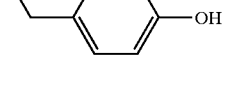 | c = 0.07, MeOH −95 |
| D-MeAla$^3$EtVal$^4$CS | —CH$_2$CH$_3$ | CH$_2$CH$_3$ | —CH$_3$ |  | c = 0.12, MeOH −145 |

TABLE III-continued

| Substance | R₁ | R₂ | R₃ | R₄ | $[\alpha]_n^{20}$ |
|---|---|---|---|---|---|
| D-MeSer³EtVal⁴CS | —CH₂CH₃ | CH₂CH₃ | —CH₂OH | isopropyl | |
| D-MeAla³EtPhe⁴CS | CH₂CH₃ | CH₂CH₃ | CH₃ | benzyl | c = 0.06, MeOH −138 |
| D-MeAla³-EtPhe⁴(4-CH₂—PO(OMe)₂ | CH₂CH₃ | CH₂CH₃ | —CH₃ | 4-(CH₂PO(OMe)₂)benzyl | |
| D-MeSer³-EtPhe⁴(4-CH₂—PO(OMe)₂ | CH₂CH₃ | CH₂CH₃ | —CH₂OH | 4-(CH₂PO(OMe)₂)benzyl | |
| D-MeAla³-EtPhe⁴(4-CH₂—PO(OH)₂ | CH₂CH₃ | CH₂CH₃ | —CH₃ | 4-(CH₂PO(OH)₂)benzyl | |
| D-MeSer³-EtPhe⁴(4-CH₂—PO(OH)₂ | CH₂CH₃ | CH₂CH₃ | —CH₂OH | 4-(CH₂PO(OH)₂)benzyl | |
| EtPhe⁴(4-CH₂—PO(OMe)₂ | CH₂CH₃ | CH₂CH₃ | —H | 4-(CH₂PO(OMe)₂)benzyl | c = 0.05, MeOH −136 |
| EtPhe⁴(4-CH₂—PO(OH)₂ | CH₂CH₃ | CH₂CH₃ | —H | 4-(CH₂PO(OH)₂)benzyl | |
| EtPhe(4-CH₂COOMe)⁴CS | CH₂CH₃ | CH₂CH₃ | —H | 4-(CH₂COOMe)benzyl | c = 0.15, MeOH −160 |
| D-MeAla³-EtPhe(4-CH₂COOMe)⁴CS | CH₂CH₃ | CH₂CH₃ | —CH₃ | 4-(CH₂COOMe)benzyl | |
| EtPhe(4-CH₂COOH)⁴CS | CH₂CH₃ | CH₂CH₃ | —H | 4-(CH₂COOH)benzyl | |

TABLE III-continued

| Substance | $R_1$ | $R_2$ | $R_3$ | $R_4$ | $[\alpha]_n^{20}$ |
|---|---|---|---|---|---|
| D-MeAla³-EtPhe(4-CH₂COOH)⁴CS | CH₂CH₃ | CH₂CH₃ | —CH₃ | 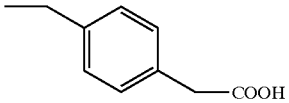 | |

What is claimed is:

1. Synthesised cyclosporin having the formula:

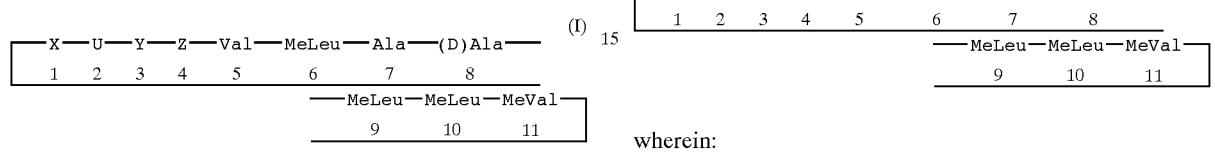

wherein:

X is -MeBmt or 6,7-dihydro-MeBmt-
U is -Abu, Nva, Val or Thr
Y is Sar or (D)-MeSer or (D)-MeAla or (D)-MeSer (OAcyl)
Z is (N-R)aa where aa={Val, Ile, Thr, Phe, Tyr, Thr (OAc), Thr (OG₁), Phe (G₂), PheCH₂(G₃) or Tyr (OG₃)} with R={alkyl>CH₃};
G₁={phenyl-COOH, phenyl-COOMe or phenyl-COOEt};
G₂={CH₂COOH, CH₂COOMe(Et)₄, CH₂PO(OMe)₂ or CH₂PO(OH)₂};
G₃={PO(OH)₂, PO(OCH₂CH=CH₂)₂, CH₂COOH, CH₂COOMe, or CH₂COOEt}.

2. Cyclosporin according to claim 1, wherein the residue Z in position 4 is (R)Val where R>CH₃ and R<C₁₀H₁₁.

3. Cyclosporin according to claim 1, wherein the residue Z in position 4 is N-ethyl-Valine.

4. Pharmaceutical composition containing the compound having the formula:

wherein:

X is -MeBmt or 6,7-dihydro-MeBmt-
U is -Abu, Nva, Val or Thr
Y is Sar or (D)-MeSer or (D)-MeAla or (D)-MeSer (OAcyl)
Z is (N-R)aa where aa={Val, Ile, Thr, Phe, Tyr, Thr (OAc), Thr (OG₁), Phe (G₂), PheCH₂(G₃) or Tyr (OG₃)} with R={alkyl>CH₃};
G₁={phenyl-COOH, phenyl-COOMe or phenyl-COOEt};
G₂={CH₂COOH, CH₂COOMe(Et), CH₂PO(OMe)₂ or CH₂PO(OH)₂};
G₃={PO(OH)₂, PO(OCH₂CH=CH₂)₂, CH₂COOH, CH₂COOMe, or CH₂COOEt}.

5. Pharmaceutical composition according to claim 4, combined with a pharmaceutically acceptable solution.

6. A medicinal product for the treatment and prevention of acquired immunodeficiency syndrome (AIDS) containing the cyclosporin according to claim 1 or claim 4.

7. A medicinal product for the treatment and prevention of AIDS containing the cyclosporin according to claim 3.

* * * * *